United States Patent
Friedman et al.

(10) Patent No.: US 11,813,471 B2
(45) Date of Patent: Nov. 14, 2023

(54) SYSTEMS AND METHODS FOR IMPLANTABLE DEVICES

(71) Applicant: Mayo Foundation for Medical Education and Research, Rochester, MN (US)

(72) Inventors: Paul A. Friedman, Rochester, MN (US); Samuel J. Asirvatham, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1302 days.

(21) Appl. No.: 16/238,374

(22) Filed: Jan. 2, 2019

(65) Prior Publication Data
US 2019/0217110 A1    Jul. 18, 2019

Related U.S. Application Data

(60) Provisional application No. 62/618,466, filed on Jan. 17, 2018.

(51) Int. Cl.
| | |
|---|---|
| *A61B 5/00* | (2006.01) |
| *A61F 7/12* | (2006.01) |
| *A61B 17/3209* | (2006.01) |
| *A61B 5/361* | (2021.01) |
| *A61N 1/39* | (2006.01) |
| *A61N 1/362* | (2006.01) |
| *A61B 18/14* | (2006.01) |
| *A61M 25/01* | (2006.01) |
| *A61M 25/10* | (2013.01) |
| *A61B 17/00* | (2006.01) |

(Continued)

(52) U.S. Cl.
CPC ........ *A61N 1/39624* (2017.08); *A61B 5/0031* (2013.01); *A61B 17/32093* (2013.01); *A61B 18/1492* (2013.01); *A61F 7/12* (2013.01); *A61M 25/0155* (2013.01); *A61M 25/10* (2013.01); *A61N 1/3622* (2013.01); *A61N 1/395* (2013.01); *A61B 5/361* (2021.01); *A61B 2017/00044* (2013.01); *A61M 2025/0024* (2013.01); *A61N 1/08* (2013.01); *A61N 1/36521* (2013.01); *A61N 1/3702* (2013.01)

(58) Field of Classification Search
CPC combination set(s) only.
See application file for complete search history.

(56) References Cited

U.S. PATENT DOCUMENTS

| | | | | |
|---|---|---|---|---|
| 6,090,145 A | * | 7/2000 | Hassler | ............... A61F 2/30721 623/23.14 |
| 2002/0198526 A1 | * | 12/2002 | Shaolian | ................ A61B 17/60 606/907 |

(Continued)

FOREIGN PATENT DOCUMENTS

WO     WO 2017/096133       6/2017

*Primary Examiner* — Joseph A Stoklosa
*Assistant Examiner* — Adam J Avigan
(74) *Attorney, Agent, or Firm* — Fish & Richardson P.C.

(57) ABSTRACT

This document describes methods and materials for reducing incision sizes for improving the treatment of pathological conditions, including arrhythmias and trauma, using temperature modulation via implantable devices. For example, this document describes methods and devices for treating atrial and/or ventricular fibrillation by cooling the epicardium.

16 Claims, 3 Drawing Sheets

(51) Int. Cl.
    *A61N 1/08*       (2006.01)
    *A61N 1/365*      (2006.01)
    *A61N 1/37*       (2006.01)
    *A61M 25/00*      (2006.01)

(56)            References Cited

U.S. PATENT DOCUMENTS

| | | |
|---|---|---|
| 2008/0195161 A1 | 8/2008 | Sakuma et al. |
| 2009/0299216 A1* | 12/2009 | Chen .................... A61B 5/031 |
| | | 600/561 |
| 2012/0053660 A1 | 3/2012 | Dobak, III |
| 2012/0277742 A1 | 11/2012 | Laufer |
| 2012/0290023 A1 | 11/2012 | Boyden et al. |
| 2015/0342675 A1 | 12/2015 | Highsmith |
| 2017/0156616 A1 | 6/2017 | Talkachova et al. |
| 2017/0224986 A1 | 8/2017 | Imran et al. |
| 2019/0216641 A1 | 7/2019 | Friedman et al. |

\* cited by examiner

SYSTEMS AND METHODS FOR IMPLANTABLE DEVICES

CROSS-REFERENCE TO RELATED APPLICATIONS

This application claims the benefit of U.S. Provisional Application Ser. No. 62/618,466, filed Jan. 17, 2018. The disclosure of the prior application is part of (and is incorporated by reference in) the disclosure of this application.

BACKGROUND

1. Technical Field

This document relates to methods and materials for reducing incision sizes for the treatment of pathological conditions, including arrhythmias and trauma, using temperature modulation via implantable devices. For example, this document relates to methods and devices for treating atrial and/or ventricular fibrillation by cooling the epicardium.

2. Background Information

Sudden cardiac arrest is the third leading cause of death of Americans, resulting in more deaths each year than Alzheimer's, assault with firearms, breast cancer, colorectal cancer, diabetes, HIV, house fires, motor vehicle accidents, prostate cancer and suicides combined. More than 350,000 people die from sudden cardiac arrest each year in the United States.

Atrial fibrillation is the most common arrhythmia encountered in clinical practice, affecting over 2.5 million Americans. The risk of atrial fibrillation increases with advancing age, with a lifetime risk of developing the arrhythmia of 25% of all men and women 40 years of age or older. A Mayo Clinic study indicated that the burden of this disease will significantly grow with 16 million Americans expected to be afflicted by 2050.

Multiple prospective randomized trials have demonstrated the clinical benefit of implantable cardiac defibrillators (ICDs) in saving the lives of at-risk individuals, leading to their wide-spread adoption. A downside associated with ICD therapy, however, is the pain associated with defibrillation, whether shocks are delivered appropriately or inappropriately.

SUMMARY

This document describes methods and materials for reducing incision sizes for improving the treatment of pathological conditions, including arrhythmias and trauma, using temperature modulation via implantable devices. For example, this document describes methods and devices for treating atrial and/or ventricular fibrillation by cooling the epicardium.

In one aspect, this disclosure is directed to a method of deploying an implantable device. The method can include creating a Z-shaped incision in a skin of a patient, inserting a tool into the Z-shaped incision, and using the tool, deploying an implantable device in a cavity of the patient. In some cases, the cavity of the patient can be a pericardium. In some cases, the Z-shaped incision can be made using a Z-plasty technique. In some cases, the method can include telescoping the tool to create incisions in a deeper tissue of the patient. In some cases, the method can include expanding a balloon coupled to the tool, where the balloon expansion opens the deeper tissue of the patient. In some cases, inserting the tool can create a horizontal slit and the implantable device can be flat, such that the horizontal slit provides access for the flat implantable device. In some cases, the method can include stacking elements of the implantable device to deploy the implantable device, and upon deployment, expanding the elements of the implantable device. In some cases, the method can include positioning a first element of the implantable device in an oblique sinus of the patient. In some cases, the method can include positioning a second element of the implantable device on an opposite side of a pericardial fold of the patient than the first element. In some cases, the implantable device can provide thermal therapy, stem cell therapy, gene therapy, and/or pharmacological agents therapy.

In another aspect, this disclosure is directed to a tool for deploying an implantable device. The tool can include an incision component, and a horizontal base that provides advancement of the implantable device. In some cases, the tool can include a telescoping component that advances the incision component to create an incision in deeper tissue. In some cases, the incision component can be configured to create a Z-shaped incision. In some cases, the tool can include a balloon. In some cases, the balloon can be expandable to create a horizontal slit opening. In some cases, the tool can include an aperture configured to receive a guidewire.

In yet another aspect, this disclosure is directed to an implantable device. In some cases, the device can include two or more therapeutic elements, and a structure coupling the two or more therapeutic elements together. In some cases, the two or more therapeutic elements can include a thermal therapy element, a stem cell therapy element, a gene therapy element, and/or a pharmacological agents therapy element. In some cases, the thermal therapy element can be a Peltier element. In some cases, the thermal therapy element can provide thermal therapy to a cardiac tissue, a nerve tissue, and/or a thoracic tissue. In some cases, the two or more therapeutic elements can define a flat shape. In some cases, the two or more therapeutic elements can be configured to be stacked for deployment of the implantable device. In some cases, the structure can be configured to cause expansion of the two or more therapeutic elements after deployment. In some cases, the structure can include end-to-end hinges that couple the two or more therapeutic elements together. In some cases, the structure can include a central wire.

In some cases, the implantable device can include spacers coupled to the two or more therapeutic elements or the structure to secure the implantable device in a desired location. In some cases, the implantable device can include expandable components coupled to the two or more therapeutic elements or the structure to secure the implantable device in a desired location. In some cases, one of the two or more therapeutic elements can be configured to be located in a first location and the other of the two or more therapeutic elements can be configured to be located in a second location. In some cases, the first location can be an oblique sinus. In some cases, the second location can be on an opposite side of a pericardial fold than the first location. In some cases, the other of the two or more therapeutic elements in the second location can provide mechanical support for the implantable device. In some cases, the other of the two or more therapeutic elements in the second location can provide cooling therapy. In some cases, the cooling therapy can be provided to a pulmonary vein or an atrial appendage.

Particular embodiments of the subject matter described in this document can be implemented to realize one or more of the following advantages. In some embodiments, heart conditions, such as arrhythmias and others, can be treated using the devices and methods provided herein. In some embodiments, arrhythmias can be treated by an implantable system for painlessly terminating arrhythmias. The devices and methods provided herein permit prompt termination of atrial fibrillation almost immediately after an episode begins (to prevent persistence) and is effective irrespective of patient age and comorbidities. In some cases, such conditions can be treated in a minimally invasive fashion using the devices and methods provide herein. Such minimally invasive techniques can reduce recovery times, patient discomfort, and treatment costs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods and examples are illustrative only and not intended to be limiting.

The details of one or more embodiments of the invention are set forth in the accompanying drawings and the description below. Other features, objects, and advantages of the invention will be apparent from the description, drawings, and from the claims.

DESCRIPTION OF DRAWINGS

Like reference numbers represent corresponding parts throughout.

DETAILED DESCRIPTION

This document describes methods and materials for reducing incision sizes for improving the treatment of pathological conditions, including arrhythmias and trauma, using temperature modulation via implantable devices. For example, this document describes methods and devices for treating atrial and/or ventricular fibrillation by cooling the epicardium.

Implantable cardiac defibrillators (ICDs) can aid saving the lives of at-risk individuals. A downside associated with ICD therapy, however, is the pain associated with defibrillation, whether shocks are delivered appropriately or inappropriately.

Some advantages of the methods and systems provided herein can include treating arrhythmias painlessly, or substantially painlessly, by an implantable system. Further, such conditions can be treated in a minimally invasive fashion using the devices and methods provide herein. Such minimally invasive techniques can reduce recovery times, patient discomfort, and treatment costs.

Figure 1:
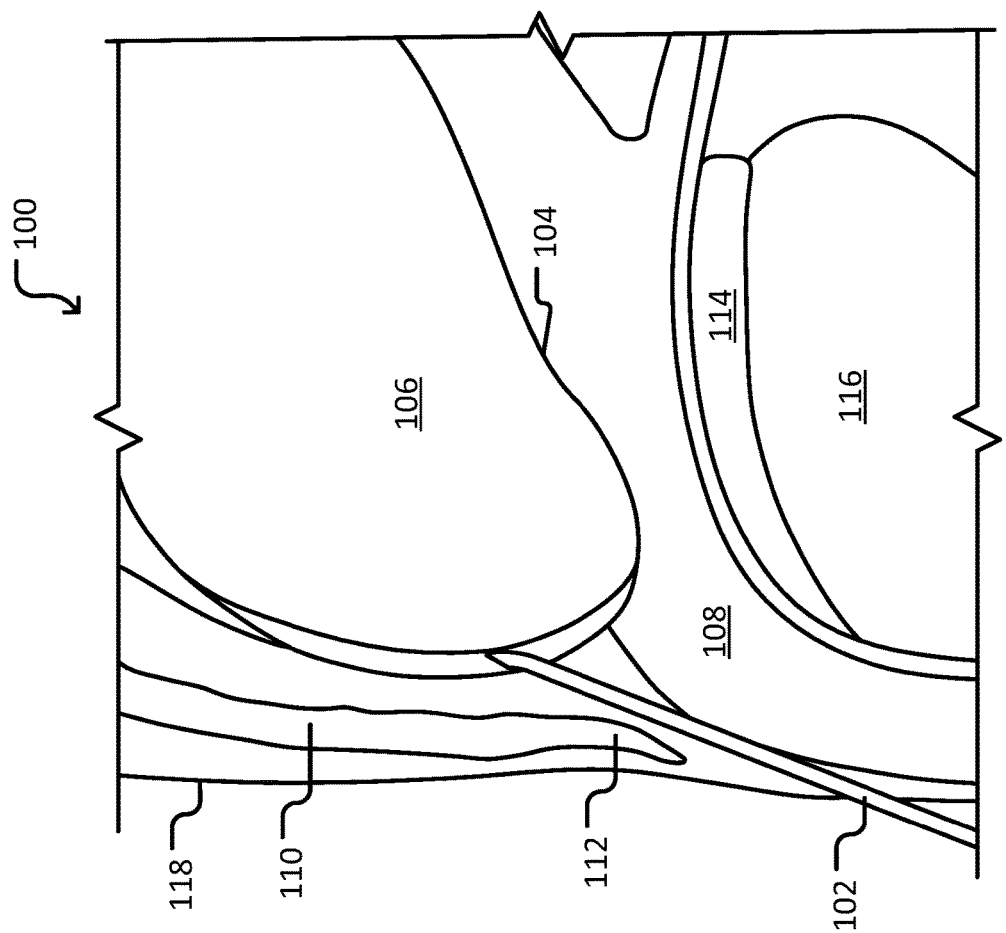
FIG. 1 is a lateral view of a device being inserted into a pericardium using a percutaneous epicardial access, in accordance with some embodiments provided herein.
Figure 5:
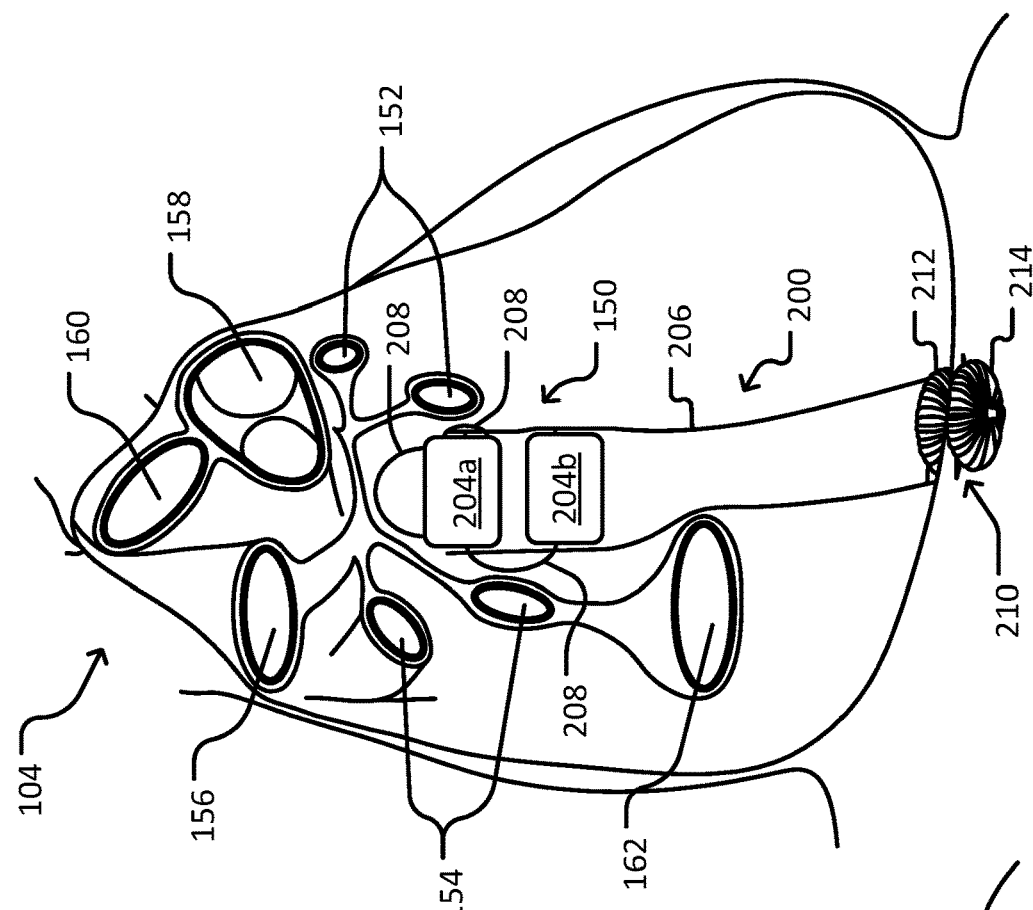
FIG. 5 is a diagram of a cooling device being implanted in a pericardium, in accordance with some embodiments provided herein.
Figure 6:
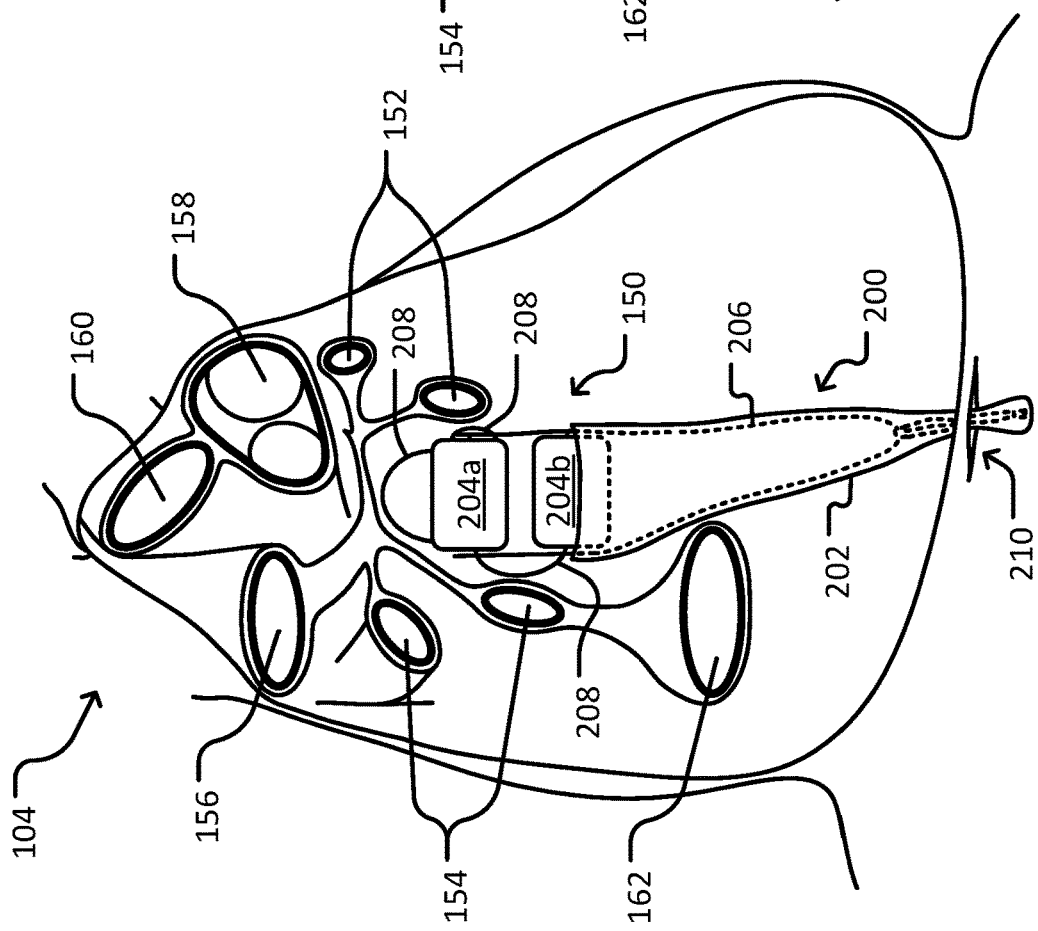
FIG. 6 is a diagram of a cooling device implanted in a pericardium, in accordance with some embodiments provided herein.

Referring to FIG. 1, a device 102 being inserted into a pericardium 104 of a heart 106 of a patient 100 using percutaneous epicardial access is shown. When inserting device 102 in patient 100, device 102 punctures skin 118 at an upward angle. Device 102 should avoid the diaphragm 108, liver 114, and stomach 116. The upward angle allows these organs to be avoided and allows device 102 to maneuver under sternum 110, specifically the xiphoid process 112.

To reduce the size of the incision for inserting device 102, a stab incision tool can be used to create a fine Z-shaped puncture and/or incision (e.g., Z-plasty incision) on skin 118 of patient 100. In some cases, the stab incision tool is Z-shaped. The Z-shaped puncture can be an ongoing Z-incision such that the thickness of the incision is split into individual layers. For example, the top and/or bottom of a Z in the Z-shaped incision may be a standard width, but by providing an angle between the top and bottom of the Z, the overall length of the incision can be reduced, while maintaining adequate access.

In some cases, device 102 is the stab incision tool. Further, the stab incision tool can be used to stretch the Z-shaped puncture into a relatively straight line, allow the incision to expand, without lengthening the incision. In some cases, the stab incision tool can be used to create a similar incision for the subcutaneous tissues. In some cases, the stab incision tool can be telescoping to create incisions in deeper tissue. In some cases, a different tool can be used to create a Z-shaped incision in the subcutaneous tissues. In some cases, the stab incision tool and/or device 102 can unfold, creating a larger entry path. For example, the incision may be about 5-10 mm, but expand to create an opening that is about 10 cm. In some cases, the stab incision tool can allow a Z-plasty incision to be made in the skin and provide a distal balloon for expansion, creating an opening in deeper tissue. In some cases, an elongated balloon (e.g., ruler shaped) can be used to create a horizontal slit to permit a flat shaped device to be advanced to the pericardial space.

Figure 2:
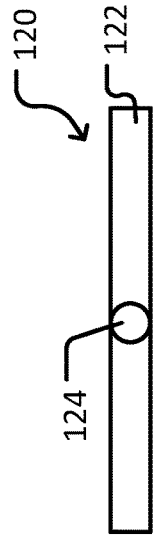
FIG. 2 is a cross-sectional view of a delivery tool, in accordance with some embodiments provided herein.
Figure 3:
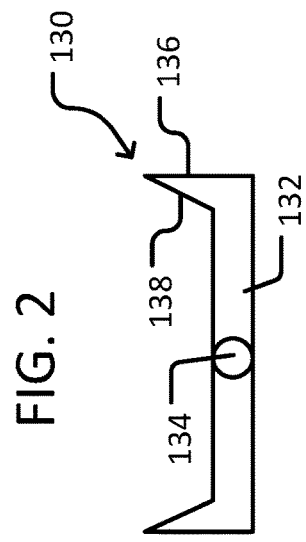
FIG. 3 is a cross-sectional view of a second delivery tool, in accordance with some embodiments provided herein.

Referring to FIGS. 2 and 3, cross sections of delivery tools 120 and 130 are shown. Delivery tools 120 and 130 include structure 122 and 132, respectively, which define a lumen 124 and 134, respectively. In some cases, the lumen is circular, oval, elliptical, etc.

In some cases, structure 122 and/or 132 can be rectangular, as shown. In some cases, structure 122 and/or 132 can be oblong, elongated, elliptical, or other shape along a cross section of the structure 122 and/or 132. In some cases, the structure 122 and/or 132 can include a taper at a proximal end, a distal end, or both. The taper can facilitate ease of access into patient 100. In some cases, delivery tool 120 can be used as a dilator prior to inserting delivery tool 130. In some cases, structure 122 and/or 132 can be used as a track to advance other tools into the pericardium. In some cases, the lumen 124 and/or 134 can receive a micropuncture needle to access the pericardial space and place a wire (e.g., a guidewire), which can alternatively be used to advance tools and devices into the pericardium. For example, a device like a plier can be used to expand the track to fit the limits of the Z-incision. In some cases, a tip of the plier can be inserted in the pericardium 104, as shown in FIG. 1, and a fulcrum for the plier can be located external to the skin insertion site. Alternatively, a non-compliant balloon can be used to expand the incision. In some cases, a flat, expandable ruler can be used as an expansion tool, either alone or in combination with a balloon. In some cases, the expansion tool can be made of nitinol, or another biomedically compatible material. In some cases, a balloon can be used in the pericardial space to serve as a space holder. This can avoid retraction of the wire when expanding the incision.

In some cases, the delivery tool 130 can also include a side protrusions 136 that defines interior edges 138. In some cases, the protrusions 136 are perpendicular to structure 132. Alternatively, the protrusions 136 can be at an angle from the structure 132. In some cases, the protrusions 136 can extend in a curved manner from the structure 132. In some cases, the interior edges 138 extend at an angle from the structure 132. In some cases, the interior edges 138 can have a radius of curvature from the structure 132 to the protrusion 136. The configuration of delivery tool 130 can aid in guiding implantable devices to the correct position by creating a track, as described above, or a trough.

These techniques can be used for insertion of cooling devices, pacemakers, and/or other implanted devices. In addition, reducing the size of the incision can be used for cosmetic surgeries, as an adjunct to the delivery of dermal and subcutaneous chemotherapy or pharmacological therapy.

Figure 4:
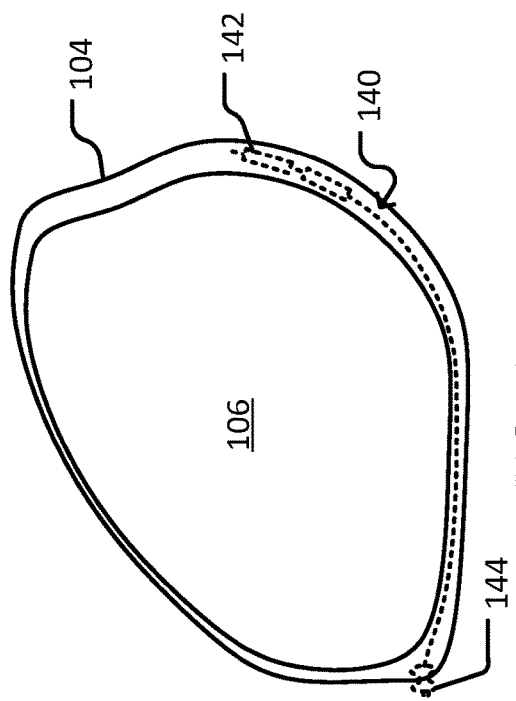
FIG. 4 is a cross-sectional view of a cooling device implanted in a pericardium of a heart, in accordance with some embodiments provided herein.

Referring to FIG. 4, a device 140 can be implanted in the pericardial space between the heart 106 and the pericardium 104. The device 140 can include a distal end 142 and a proximal end 144. In some cases, the distal end 142 can include therapeutic devices, such as cooling devices. In some cases, the proximal end 144 can include a fastening device to secure device 140 to the pericardium 104.

Referring to FIGS. 5-8, a cooling device 200 implanted in a pericardium 104 of a heart is shown. As shown, the cooling device 200 can be located in the oblique pericardial sinus 150. In some cases, the cooling device 200 can include a plurality of cooling elements 204a, 204b, 204c, and/or 204d.

In some cases, the cooling device 200 can be inserted into the pericardium 104 with the aid of a delivery tool 202. The cooling device 200 and/or the delivery tool 202 can be inserted into the pericardium 104 via aperture 210. Aperture 210 can be made using the techniques and devices described herein. In some cases, delivery tool 202 can be used to maintain a condensed structure of the cooling device 200 during implantation. For example, the delivery tool 202 can contain the cooling device 200 before deployment into an implantation location. In some cases, the delivery tool 202 can limit the ability of shape memory characteristics of the cooling device 200 during deployment. In some cases, the cooling elements 204a, 204b, 204c, and/or 204d can be Peltier elements. Peltier elements can cause changes to the pericardium by fibrosis, cooling at the location of the cooling element 204a, 204b, 204c, and/or 204d.

In some cases, the cooling device 200 and the cooling elements 204a, 204b, 204c, and/or 204d can be configured such that one cooling element (e.g., cooling element 204a, 204b, 204c, and/or 204d can be received by another cooling element (e.g., cooling element 204a, 204b, 204c, and/or 204d). In some cases, the cooling element can include an excavation, an offset, or anther configuration such that a first cooling element (e.g., cooling element 204a) in a series of cooling elements can provide a space to fit an edge of a second element, and so forth. In some cases, this configuration can reduce a width, a length, and/or a height of cooling device 200, such that more elements can be placed in a reduced size of an incision of the skin, subcutaneous tissue, and/or pericardial tissue.

In some cases, elements of cooling device 200 can stack vertically to create a substantially flat elongated shape (e.g., a rule shape). The cooling device 200 can be delivered to the pericardium in the substantially flat elongated shape. In some cases, upon delivery, or other actions (e.g., shape memory, ratcheting, other device manipulation, etc.), the elements of cooling device 200 can expand (e.g., vertically, horizontally, etc.).

In some cases, the cooling device 200 can be individual elements that can be passed separately into the oblique sinus 150, or another space of the pericardium 104. The individual elements can be assembled together in the pericardium. In some cases, the elements can be assembled with the aid of magnets, wire, or leveraging of pericardial space to guide elements together. In some cases, pliers can be used to tighten elements together. In some cases, distal elements of the plier may be expandable, or take a balloon, that could be detachable from the plier to aid in anchoring the cooling device 200.

In some cases, the cooling elements 204a, 204b, 204c, and/or 204d can be individual elements that are coupled with a hinge attaching elements end-to-end. The cooling elements 204a, 204b, 204c, and/or 204d can also be attached with a central wire. In this configuration, the cooling device 200 would function similar to an accordion, except with a free margin to two parallel elements. Accordingly, the cooling device 200 can be expanded into a long, narrow device for deployment, and subsequently compressed to fit into a designated space (e.g., the oblique pericardial sinus 150). In some cases, the cooling elements 204a, 204b, 204c, and/or 204d may be deployed as a linear arrangement, but can be arranged (e.g., compressed, stacked, etc.) such that the cooling elements 204a, 204b, 204c, and/or 204d have an increased height or thickness).

In some cases, the cooling elements 204a, 204b, 204c, and/or 204d can be locked together. In some cases, a tool can be used to lock the cooling elements 204a, 204b, 204c, and/or 204d together. In some cases, compression can cause cooling elements 204a, 204b, 204c, and/or 204d to lock together. In some cases, a relationship between the cooling elements 204a, 204b, 204c, and/or 204d and the pericardial space may naturally lock the cooling elements 204a, 204b, 204c, and/or 204d together, or in a specific location.

Still referring to FIGS. 5-8, in some cases, the cooling devices can include a sensor and/or electrode (not shown) to provide feedback. The sensors can provide information regarding cooling efficacy, unwanted heating, direct electrical and biological feedback, information regarding adjacent nervous tissue, etc. In some cases, the cooling elements 204a, 204b, 204c, and/or 204d can include thermal insulation elements to prevent injury to surrounding structures (e.g., esophagus, vagus nerve, phrenic nerve, etc.). In some cases, an impedance sensor, and/or an electrode, can be used in the pericardial space. The impedance sensor and/or electrode can be used to diagnose fibrillation, separately or in addition to another device (e.g., as a double-check). In some cases, the impedance sensor and/or electrode can detect atrial and/or ventricular fibrillation. In some cases, the impedance sensor and/or electrode can record neural signals (e.g., non-myocardial signals).

Cooling device 200 (e.g., cooling elements 204a and 204b) can be implanted in the oblique pericardial sinus 150. Specifically, cooling device 200 can be located in the pericardium 104 between the left pulmonary veins 152 and the right pulmonary veins 154. Cooling device 200 can further be positioned below the superior vena cava 156, the left pulmonary artery 158, and the ascending aorta 160, and above the inferior vena cava 162.

In some cases, to achieve the desired placement, spacers can be delivered and positioned in the pericardium 104 (e.g., in the oblique pericardial sinus 150). In some cases, the spacer can be an expandable element. The spacer can be non-erosive. In some cases, the spacer is delivered with the cooling device 200. Alternatively, the spacer can be delivered separately from the cooling device 200.

In some cases, phalanges 208 can be used to secure the cooling device 200 in the desired location (e.g., the oblique pericardial sinus 150). In some cases, phalanges 208 are naturally recoiling phalanges that are attached to the device, but coil into spaces of the pericardium 104 (e.g., oblique pericardial sinus 150), providing fixation of the cooling device 200 in the pericardium 104.

Wires 206 can extend from the cooling elements 204a and 204b towards pericardium 104. In some cases, wires 206 can be antennas (e.g., an inductive antenna), such that cooling device 200 can communicate remotely. In some cases, remote communication can be with a device (e.g., a pulse generator) internal to the patient. In some cases, remote communication can be with a device (e.g., a power source, a controller, etc.) external to the patient. In some cases, wire 206 runs through aperture 210 to other areas of the body (e.g., skin 118 of FIG. 1) or a generator (e.g., to power cooling device 200).

In some cases, wires 206 can be used to secure cooling device 200 to pericardium 104. In some cases, small clips can be placed on the edges of aperture 210. A ring-shaped suture (e.g., securing elements 212 and/or 214) can be placed over a number of the clips, with overhanging wires to enclose the aperture 210. In some cases, a cryo element can be used to close aperture 210. In some cases, the cooling elements 204a, 204b, 204c, and/or 204d can be used to power the cryo element to gain fixity and closure of aperture 210. In some cases, the cooling elements 204a, 204b, 204c, and/or 204d can be used to gain fixity of the individual element to the overlying tissue (e.g., atrial myocardial fat) by cryo welding, preventing displacement. In some cases, to close aperture 210, opposing balloons or expandable elements may be used along wire 206.

While the methods and devices for closing aperture 210 are described with respect to securing cooling device 200 in the pericardium 104, similar methods and devices can be used to create a reservoir for stem cells, gene therapy, other devices, and/or slow release pharmacological agents. Similarly, punctures into the pleural space, or other extrapericardial mediastinal spaces may be used by create an enclosed space, as described herein. Further, the closure techniques may be used in other situations, such as, closing transapical puncture sites, pericardial access sites, atrial septal defects, or other cardiac defects (e.g., purposeful or inadvertent cardiac puncture).

Figure 7:
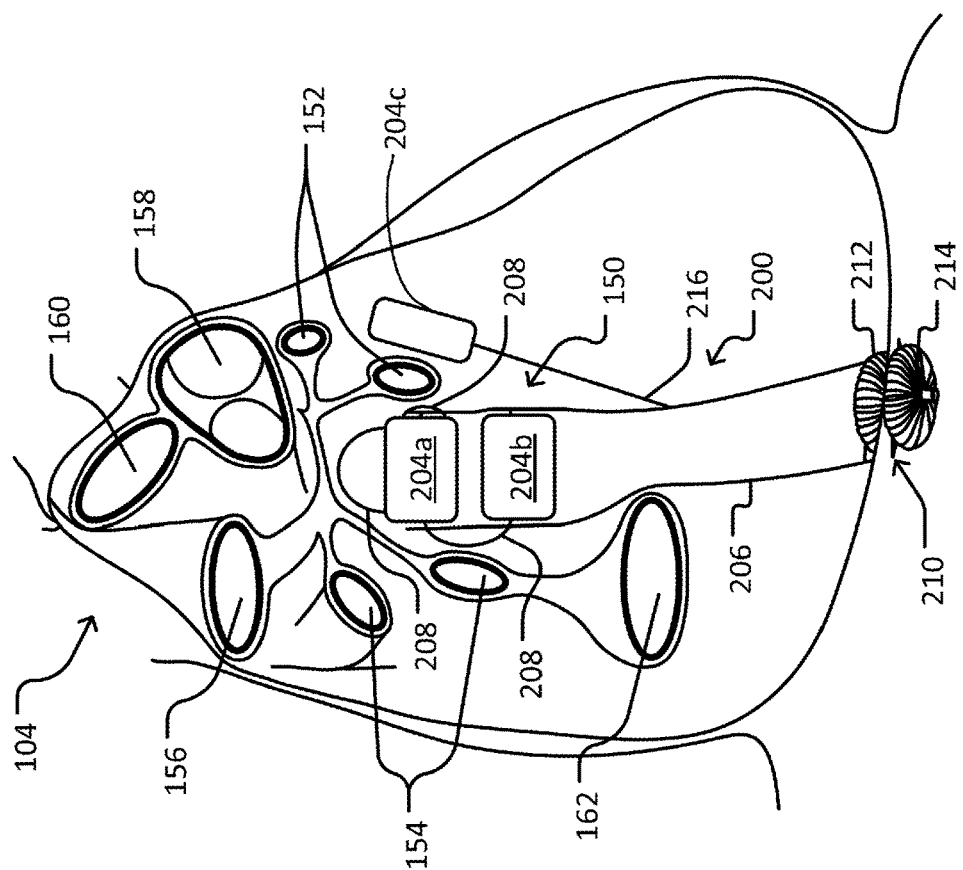
FIG. 7 is a diagram of a second cooling device implanted in a pericardium, in accordance with some embodiments provided herein.

As shown in FIG. 7, the cooling device 200 can include an arm 216 that extends toward cooling elements 204c and/or 204d from wire 206. Arm 216 can naturally be drawn toward elements 204a and/or 204b (e.g., via shape memory techniques, a clip design, a spring, etc.). Arm 216 can aid in securing cooling element 204c on an opposite side of the left pulmonary veins 152 than the oblique pericardial sinus 150. In some cases, cooling element 204c can be fixed in place using cryo welding, as described above. In some cases, cooling element 204c can be inactive and function solely to provide mechanical stability to cooling device 200.

Figure 8:
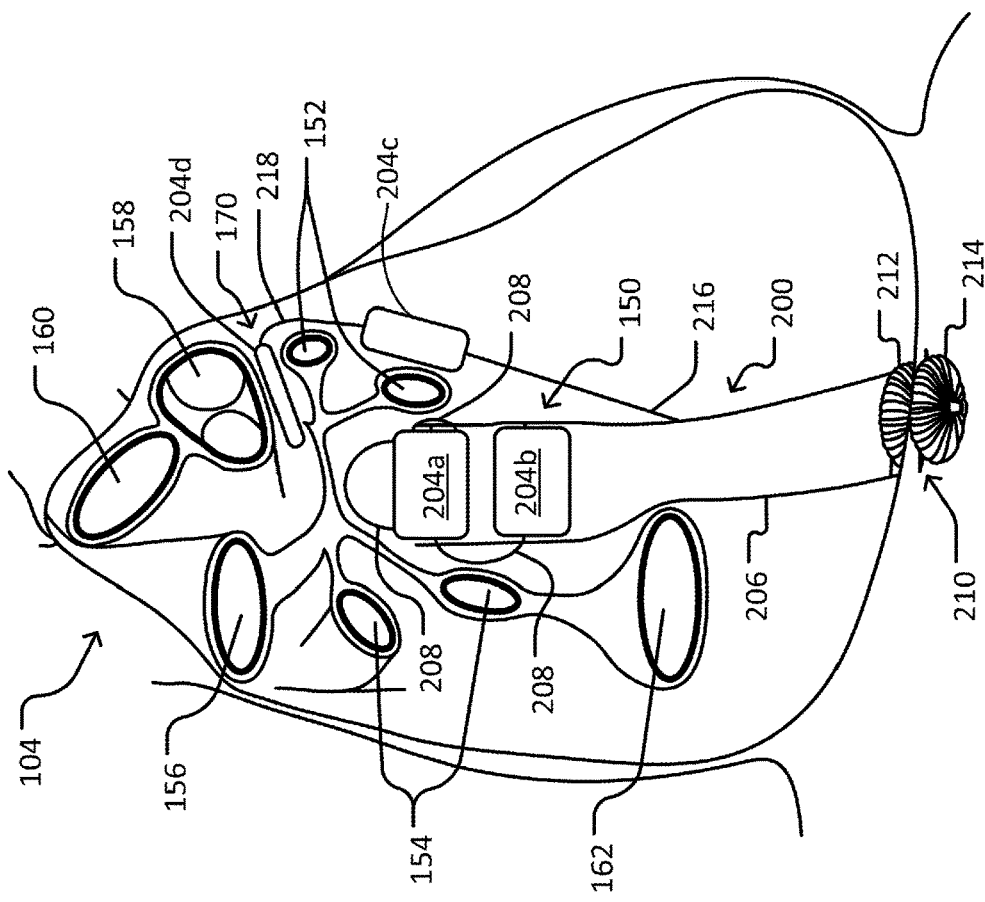
FIG. 8 is a diagram of a third cooling device implanted in a pericardium, in accordance with some embodiments provided herein.

As shown in FIG. 8, the cooling device 200 can include an arm 218 that extends from cooling element 204c towards cooling element 204d. Arm 218 can naturally be drawn toward elements 204a, 204b, and/or 204c (e.g., via shape memory techniques, a clip design, a spring, etc.). Arm 218 can aid in securing cooling element 204d in a transverse sinus 170 of the patient. In some cases, cooling element 204d can be fixed in place using cryo welding, as described above. In some cases, cooling element 204d can be inactive and function solely to provide mechanical stability to cooling device 200.

In some cases, the arrangement of cooling elements 204a, 204b, 204c, and/or 204d may be different based on the targeted areas of cooling. In some cases, cooling elements 204a, 204b, 204c, and/or 204d may provide cooling of the vein of Marshall, the oblique pericardial sinus 150, the transverse sinus 170, pulmonary veins 152/154, atrial appendages, other cardiac tissue, nerves, and/or central thoracic tissues.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the process depicted in the accompanying figures do not necessarily require the particular order shown, or sequential order, to achieve desirable results. In certain implementations, multitasking and parallel processing may be advantageous.

What is claimed is:

1. A method of deploying an implantable device, the method comprising:

creating a Z-shaped incision in a skin of a patient;
inserting a delivery tool through the Z-shaped incision; and
using the delivery tool, deploying an implantable device in a cavity of the patient,
wherein the Z-shaped incision is created using the delivery tool.

2. A method of deploying an implantable device, the method comprising:
creating a Z-shaped incision in a skin of a patient;
inserting a delivery tool through the Z-shaped incision;
using the delivery tool, deploying an implantable device in a cavity of the patient; and
using the delivery tool, to creating incisions in a deeper tissue of the patient.

3. The method of claim 2, wherein the method further comprises expanding a balloon coupled to the delivery tool, wherein the expanding of the balloon opens the deeper tissue of the patient.

4. The method of claim 1, wherein inserting the delivery tool creates a flat horizontal slit and the implantable device is flat-shaped, such that the flat horizontal slit provides access for the flat-shaped implantable device.

5. The method of claim 1, further comprising stacking elements of the implantable device to deploy the implantable device, and upon deployment, expanding the elements of the implantable device.

6. The method of claim 1, further comprising positioning a first element of the implantable device in an oblique sinus of the patient, and positioning a second element of the implantable device on an opposite side of a pericardial fold of the patient than the first element.

7. The method of claim 1, wherein the inserting the delivery tool through the Z-shaped incision comprises stretching the Z-shaped incision in the skin into a relatively straight line during the inserting.

8. A method of deploying an implantable device, the method comprising:
creating a Z-shaped incision in a skin of a patient;
inserting a delivery tool through the Z-shaped incision; and
using the delivery tool, deploying an implantable device in a cavity of the patient,
wherein the cavity of the patient comprises an oblique sinus.

9. The method of claim 8, wherein the implantable device comprises a cooling device that is deployed in the oblique sinus.

10. The method of claim 9, wherein the deploying the implantable device comprises advancing the cooling device through an opening in a lower portion of a pericardium.

11. The method of claim 9, wherein the cooling device comprises a Peltier element.

12. The method of claim 9, wherein the cooling device comprises one or more fixation elements for securing the cooling device in the oblique sinus.

13. The method of claim 9, wherein the implantable device includes one or more electrodes or impedance sensors used to detect fibrillation.

14. The method of claim 1, wherein the Z-shaped incision is created just below a xiphoid process of the patient.

15. The method of claim 1, wherein the Z-shaped incision is created using a stab incision tool.

16. The method of claim 15, wherein the stab incision tool is Z-shaped.

* * * * *